United States Patent
Betro et al.

(10) Patent No.: US 9,562,824 B2
(45) Date of Patent: *Feb. 7, 2017

(54) MEASURING MOISTURE LEAKAGE THROUGH LIQUID-CARRYING HARDWARE

(71) Applicant: International Business Machines Corporation, Armonk, NY (US)

(72) Inventors: Michael G. Betro, Pleasant Valley, NY (US); Michael J. Ellsworth, Jr., Lagrangeville, NY (US); Enrico A. Romano, Wingdale, NY (US); Prabjit Singh, Poughkeepsie, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/070,698

(22) Filed: Mar. 15, 2016

(65) Prior Publication Data

US 2016/0178473 A1 Jun. 23, 2016

Related U.S. Application Data

(63) Continuation of application No. 14/558,807, filed on Dec. 3, 2014.

(51) Int. Cl.
*G01M 3/20* (2006.01)
*G01M 3/00* (2006.01)
(Continued)

(52) U.S. Cl.
CPC ............... *G01M 3/20* (2013.01); *G01M 3/002* (2013.01); *G01M 3/02* (2013.01); *G01N 15/0806* (2013.01);
(Continued)

(58) Field of Classification Search
CPC .......... G01M 3/002; G01M 3/02; G01M 3/20; G01N 15/0806; G01N 27/12; G01N 27/223; G01N 27/605; G01N 2223/647; G01N 19/10; G01N 33/0016; G01N 33/0036
(Continued)

(56) References Cited

U.S. PATENT DOCUMENTS 3,286,509 A * 11/1966 Gluckman ............. G01N 15/08
73/38
4,572,427 A * 2/1986 Selfridge ................. A01C 1/02
165/146

(Continued)

OTHER PUBLICATIONS

"W3/330 Water Vapor Transmission Rate Test System", Labthink, The Ultimate Testing Technology, provided in Post Disclosure on Nov. 15, 2013, retrieved on Oct. 2, 2014, <http://www.labthink.cn/en/product-info-water-vapor-transmission-rate-test-system-w3-330.html>.

(Continued)

*Primary Examiner* — Michael A Lyons
*Assistant Examiner* — David L Singer
(74) *Attorney, Agent, or Firm* — Brian M. Restauro (57) ABSTRACT

Embodiments of the present invention provide moisture measuring systems and methods. According to one embodiment of the present invention, a sealable compartment is used in which a specimen containing liquid can be inserted, such that all of the specimen is contained within the compartment. The relative humidity in the compartment is measured over a duration of time, which can be used to calculate the amount of liquid leaked by the specimen. Embodiments of the present invention can be utilized, for example, to calculate the leakage rate of water-carrying hardware of a cooling system, without having to create a membrane or other isolated sample of materials.

1 Claim, 5 Drawing Sheets (51) Int. Cl.
*G01N 19/10* (2006.01)
*G01N 27/22* (2006.01)
*G01M 3/02* (2006.01)
*G01N 15/08* (2006.01)
*G01N 33/00* (2006.01)

(52) U.S. Cl.
CPC ............ *G01N 19/10* (2013.01); *G01N 27/223* (2013.01); *G01N 33/0016* (2013.01); *G01N 33/0036* (2013.01)

(58) Field of Classification Search
USPC ....... 73/29.01, 29.02, 38, 40, 40.7, 47, 49.3, 73/73, 865.8, 866
See application file for complete search history.

(56) References Cited

U.S. PATENT DOCUMENTS

| | | | |
|---|---|---|---|
| 4,711,118 A | 12/1987 | Bossard et al. | |
| 5,016,468 A | 5/1991 | Jennings | |
| 5,138,643 A * | 8/1992 | Sakamoto | G03F 7/70008 378/34 |
| 5,837,888 A | 11/1998 | Mayer et al. | |
| 5,907,091 A | 5/1999 | Pause | |
| 6,354,138 B1 * | 3/2002 | Ascheman | G01N 15/0826 73/1.06 |
| 6,640,615 B1 * | 11/2003 | Morrow | G01N 15/082 73/38 |
| 6,804,989 B2 | 10/2004 | Bujas et al. | |
| 6,964,191 B1 | 11/2005 | Tata | |
| 7,299,681 B2 | 11/2007 | Cummings | |
| 7,624,622 B1 * | 12/2009 | Mayer | G01N 7/14 73/38 |
| 7,739,057 B2 | 6/2010 | Nörenberg | |
| 2004/0079136 A1 | 4/2004 | Pillion | |
| 2004/0177676 A1 | 9/2004 | Moore | |
| 2006/0032293 A1 * | 2/2006 | Wild | G01N 33/14 73/38 |
| 2008/0202213 A1 * | 8/2008 | Villers | G01M 3/3272 73/49.3 |
| 2008/0295578 A1 * | 12/2008 | Bothe | G01N 5/025 73/38 |
| 2010/0294025 A1 | 11/2010 | Omori et al. | |
| 2011/0252899 A1 * | 10/2011 | Felts | C23C 16/045 73/865.8 |
| 2016/0161357 A1 | 6/2016 | Betro et al. | |

OTHER PUBLICATIONS

IBM Appendix P.: "List of IBM Patents or Patent Applications to Be Treated as Related", Dated Sep. 27, 2016, 2 pages.

* cited by examiner

MEASURING MOISTURE LEAKAGE THROUGH LIQUID-CARRYING HARDWARE

BACKGROUND OF THE INVENTION

The present invention relates generally to the field of moisture leakage, and more particularly to measuring moisture leakage through water-carrying hardware.

Computer processor speeds have increased in recent years. Typically, air moved by fans is used to cool these computer processors. With the increase of computer processor speeds, the heat produced by processors has also increased along with the noise generated by the equipment (e.g., fans) used to cool those processors. Water cooling, as applied to computers, refers to a method used to lower temperatures of computer processors using water rather than air as the cooling medium. Because water can conduct heat about 30 times faster than air, water cooling can allow computer processors to run at higher speeds and reduce noise produced by cooling equipment.

The ability of water cooling hardware systems to cool computer hardware can be diminished, or even lost, as water permeates through, or leaks past, various materials and/or connections of materials. Determining a rate of loss of coolant from the cooling system can help designers of these water cooling hardware systems determine maintenance procedures for these systems.

SUMMARY

According to one aspect of the present invention, a moisture measuring apparatus is provided, comprising: a chamber having one or more walls that define a compartment; a relative humidity probe disposed in a wall of the chamber, wherein at least a portion of the relative humidity probe is disposed within the compartment and is configured to measure relative humidity within the compartment; a first opening disposed in a wall of the chamber, wherein the first opening is configured to receive a hose; a second opening disposed in a wall of the chamber for inserting a specimen containing liquid, such that all of the specimen is contained within the compartment; a removable cover configured to seal the second opening when coupled to the chamber; and a computer system operatively connected to the relative humidity probe, wherein the computer system is configured to receive data signals from the relative humidity probe and calculate an amount of liquid leaked by the specimen.

According to another aspect of the present invention, there is provided a method for calculating an amount of liquid leaked by a specimen, the method comprising: providing a chamber having one or more walls that define a compartment; providing a relative humidity probe disposed in a wall of the chamber, wherein at least a portion of the relative humidity probe is disposed within the compartment and is configured to measure relative humidity within the compartment; providing a first opening disposed in a wall of the chamber, wherein the first opening is configured to receive a hose; providing a second opening disposed in a wall of the chamber for inserting a specimen containing liquid, such that all of the specimen is contained within the compartment; providing a removable cover configured to seal the second opening when coupled to the chamber; providing a computer system operatively connected to the relative humidity probe, wherein the computer system is configured to receive data signals from the relative humidity probe and calculate an amount of liquid leaked by the specimen; inserting a specimen into the compartment through the second opening; drying the compartment with one or more gases inputted into the compartment through the first opening; and calculating, by the computer system, an amount of liquid leaked by the specimen based on change in percent relative humidity measured by the relative humidity probe.

DETAILED DESCRIPTION

Embodiments of the present invention recognize the need to provide more efficient systems and methods for calculating a rate of loss of coolant from water cooling hardware systems. Typically, the rate of loss of coolant through a material is determined by creating a membrane and measuring the permeation rate of water across that membrane. In some instances, creating a membrane of a material may prove costly, lead to inaccurate results, and thus increase the time it takes to determine the rate of loss of coolant. Embodiments of the present invention provide efficient and cost-effective systems and methods for calculating the leakage rate of coolant without having to create a membrane of the water cooling hardware. In this manner, as discussed in greater detail later in this specification, embodiments of the present invention can be used to calculate the leakage rate of coolant by measuring the rate at which relative humidity changes over a duration of time.

Figure 1:
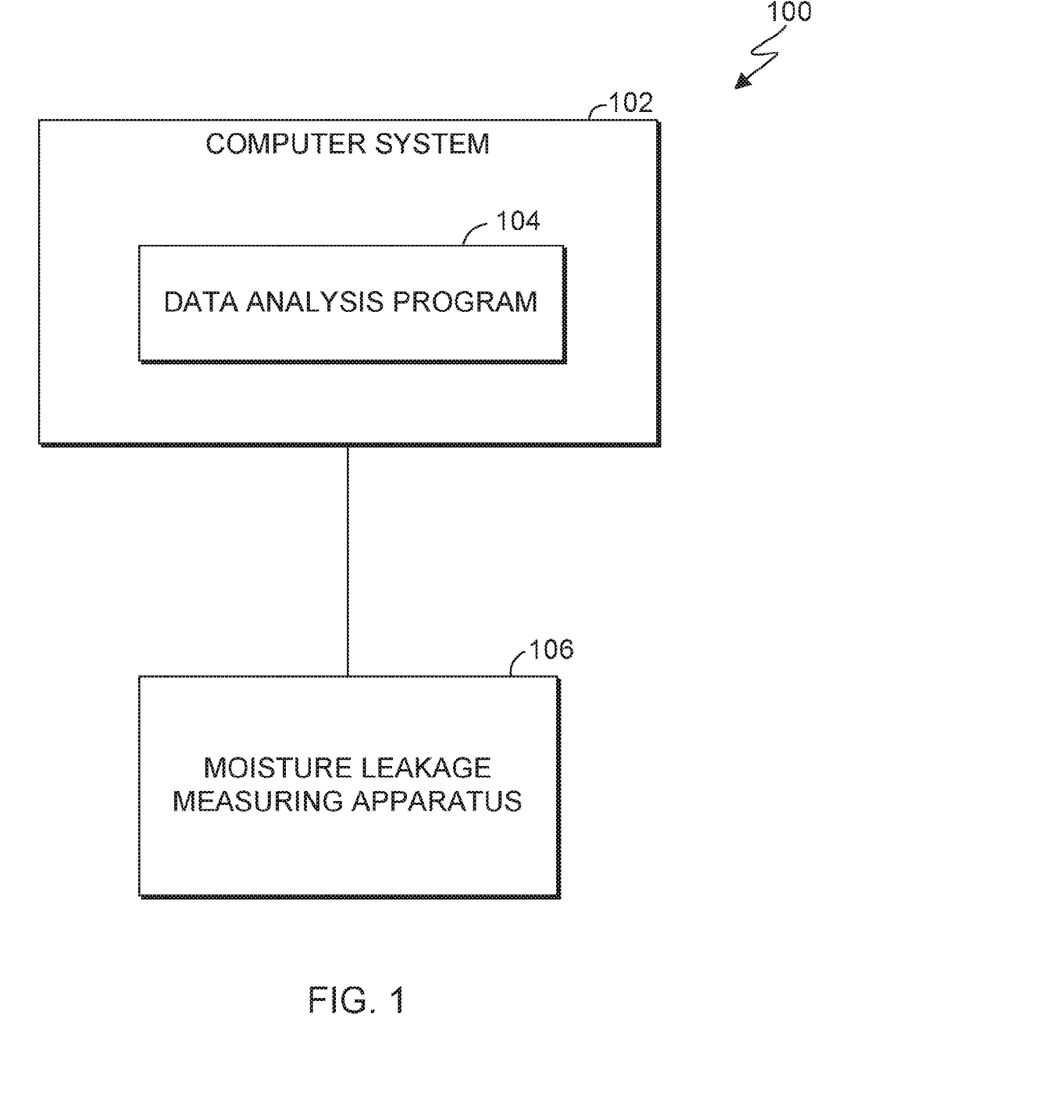
FIG. 1 is a block diagram of a moisture leakage measuring system, in accordance with an embodiment of the present invention.

FIG. 1 is a functional block diagram of moisture leakage measuring system 100, in accordance with an embodiment of the present invention. Moisture leakage measuring system 100 includes computer system 102 and moisture leakage measuring apparatus 106. In some embodiments, computer system 102 can be an integrated, onboard component of moisture leakage measuring apparatus 106. In general, computer system 102, is representative of any electronic devices, or combination of electronic devices, capable of executing machine-readable program instructions, as described in greater detail with regard to FIG. 4.

Computer system 102 includes data analysis program 104. Data analysis program 104 calculates the rate of loss of leakage of a specimen within moisture leakage measuring apparatus 106 from received data transmitted by moisture leakage measuring apparatus 106 via data cable 120, as discussed in greater detail with regard to FIG. 3. The phrase "leakage", as used herein, refers to the amount of liquid that permeates through the specimen over a duration of time, or may be the amount of liquid that leaks between two junctions of the specimen (e.g., between one or more fittings and/or couplings). Data transmitted by moisture leakage measuring apparatus 106 can include measurements of both relative humidity and temperature in the air. Data analysis program 104 can be implemented with any computer program that can mine, alter, manage, and/or retrieve data from a variety of sources and perform statistical analysis on it.

Figure 2A:
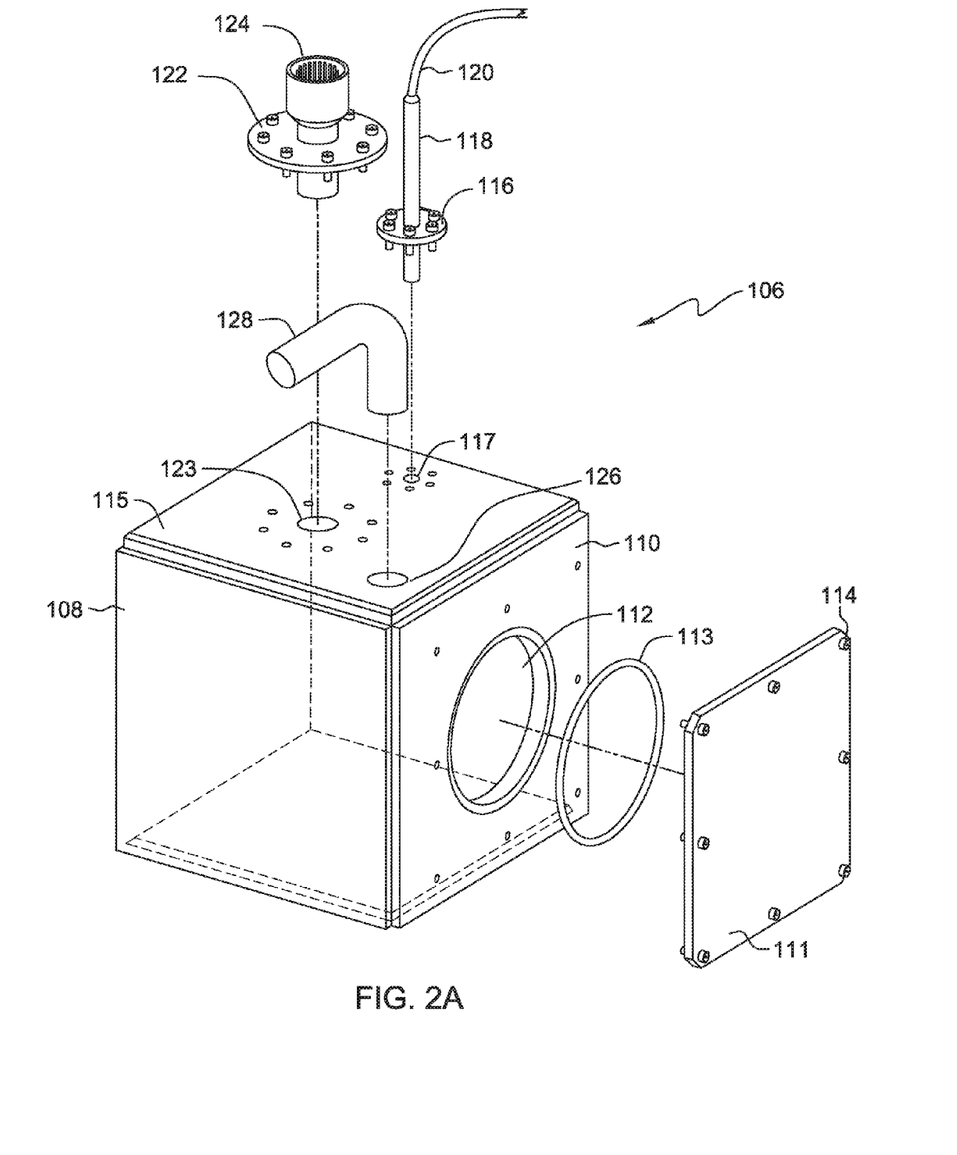
FIG. 2A is an exploded view of a moisture leakage measuring apparatus, in accordance with an embodiment of the present invention.

FIG. 2A is an exploded perspective view of moisture leakage measuring apparatus 106. Moisture leakage measuring apparatus 106 includes chamber 108. In this embodiment, chamber 108 is an enclosure forming a compartment having sidewalls. In other embodiments, moisture leakage measuring apparatus 106 can have other shapes. In general, moisture leakage measuring apparatus 106 can be made to any specification optimal to fit specimen 132 (e.g., a water-carrying component). In this embodiment, chamber 108 is made of metal that is impermeable to water and does not absorb water (i.e., is hydrophobic). Other embodiments can include a different metal or a combination of one or more metals.

Figure 2B:
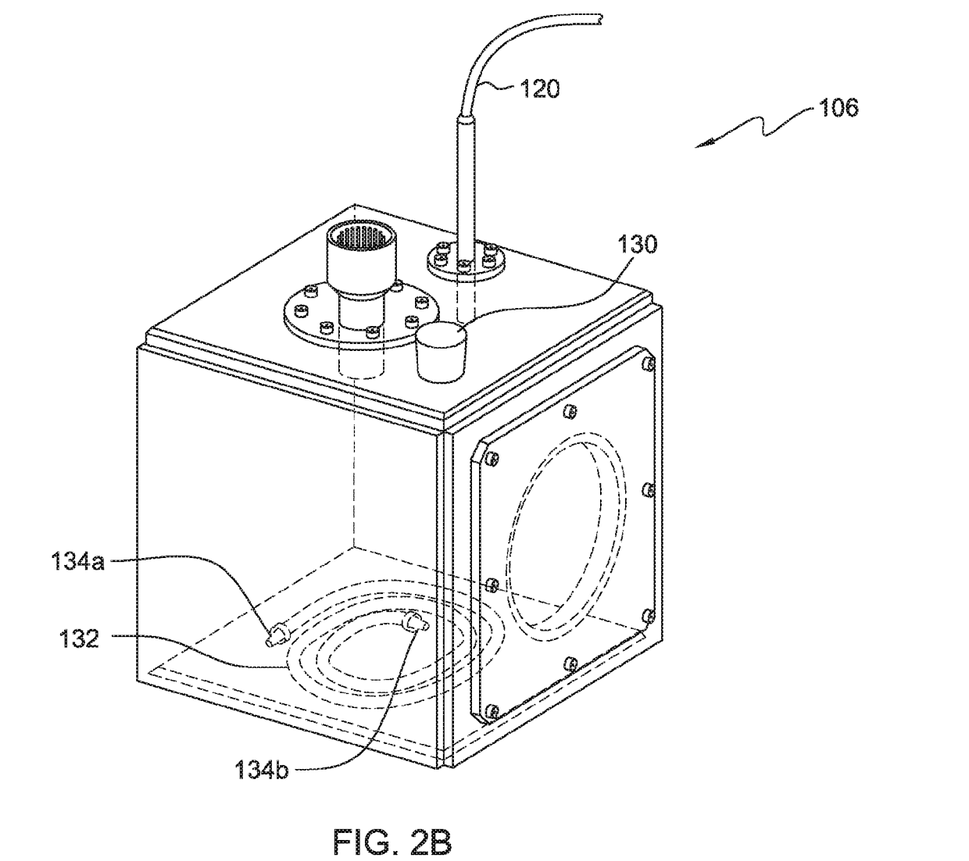
FIG. 2B is an assembled view of the moisture leakage measuring apparatus of FIG. 2A, in accordance with an embodiment of the present invention.

Chamber 108 includes opening 112 disposed in sidewall 110 of chamber 108. In this embodiment, opening 112 is circular. In general, opening 112 can be shaped to any specification optimal to fit specimen 132, which is shown in FIG. 2B. Opening 112 is sealed with gasket 113 and removable cover 111. Removable cover 111 covers opening 112 and gasket 113, sealing opening 112, and is coupled to chamber 108 by a series of fasteners 114 disposed along the perimeter of removable cover 111. In this embodiment, fasteners 114 are screws. In other embodiments, fasteners 114 can be implemented with any combination of screws, latches, bolts, washers, nuts, and/or threads. In this embodiment, removable cover 111 is a plate made of metal impermeable to water. In one embodiment, aluminum is used. Other embodiments can include a different metal or a combination of one or more metals. Similarly, in other embodiments, removable cover 111 can have other shapes, and can be coupled to chamber 108 in other ways (e.g., threading into corresponding threads within opening 112).

Chamber 108 includes opening 117 disposed in top sidewall 115 of chamber 108 in which relative humidity (RH) probe 118 is inserted. In general, RH probe 118 measures the relative humidity of a given volume. In this embodiment, RH probe 118 measures the relative humidity of the volume of the compartment formed by chamber 108. In this embodiment, RH probe 118 is inserted through opening 117 and a portion of RH probe 118 is disposed within the compartment. In this embodiment, RH probe 118 is coupled to top sidewall 115 of chamber 108 by flange 116, which seals chamber 108 preventing leakage from specimen 132 from leaving chamber 108 and preventing unwanted moisture not attributable to specimen 132. RH probe 118 collects and transmits data to computer system 102 via data cable 120. RH probe 118 can be implemented with any suitable RH probe known in the art.

Data cable 120 can be, for example, an Ethernet cable, a token ring cable, a coaxial cable, or serial cable. In general, data cable 120 can be any combination of connections that will support communications between RH probe 118 and computer system 102, in accordance with a desired embodiment of the invention.

In certain embodiments, chamber 108 includes opening 123 disposed in top sidewall 115 through which electrical feed through 124 is inserted. In this embodiment, when electrical feed through 124 is inserted through opening 123, a portion of electrical feed through 124 is disposed in the compartment formed by chamber 108. Electrical feed through 124 can be attached to one or more electric devices that can measure one or more variables being tested. For example, electrical feed through 124 can be attached to a thermocouple to measure temperature changes, or an atmospheric gauge to measure atmospheric changes. In this embodiment, electrical feed through 124 is coupled to top sidewall 115 of chamber 108 by flange 122.

Chamber 108 includes opening 126 disposed in top sidewall 115 in which hose 128 is inserted. In this embodiment, when hose 128 is inserted into opening 126, a portion of hose 128 is inserted into the compartment formed by chamber 108. Hose 128 is used to pump gas into chamber 108 to dry the compartment of chamber 108, including the inner surfaces of the sidewalls and removable cover 111. In this embodiment, the gas used to dry the inner walls of the compartment of chamber 108 is nitrogen. In other embodiments, other gases, and combinations thereof, can be used.

FIG. 2B is an assembled view of moisture leakage apparatus 106. For illustrative purposes, some elements of moisture leakage measuring apparatus 106 are not shown in FIG. 2B. As shown, plug 130 seals opening 126 (i.e., hermetically) where hose 128 is inserted, after hose 128 is removed from opening 126.

Specimen 132 is placed in the compartment of chamber 108. In this embodiment, specimen 132 is a 14 foot coiled hose with a ⅜ inch opening on both ends of the hose. The openings are closed at both ends with plugs 134a-b. In this embodiment, plugs 134a-b are hose barbs and NPT threaded plugs. In other embodiments, plugs 134a-b can be any components used to prevent water from draining from specimen 132. In general, specimen 132 can comprise any carrying hardware (e.g., enclosures used for liquid submersion cooling, a water block, etc.), filled with liquid (e.g., water, dielectric liquids, liquid nitrogen, liquid helium, antifreeze, etc.), and sealed.

Figure 3:
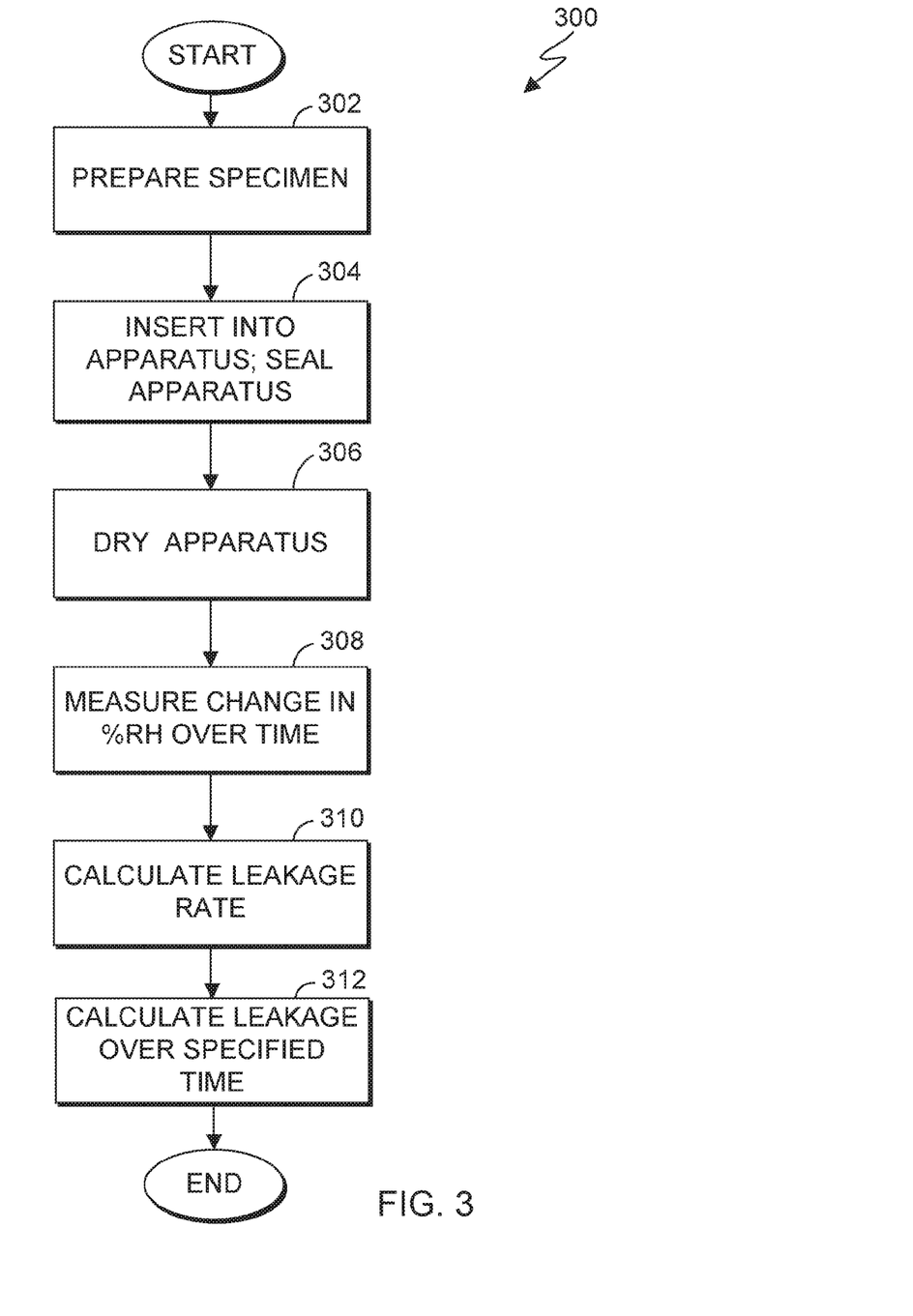
FIG. 3 is a flowchart illustrating operational steps for calculating loss of liquid from a liquid-carrying apparatus, in accordance with an embodiment of the present invention.

FIG. 3 is a flowchart 300 illustrating operational steps for calculating loss of liquid from a liquid-carrying apparatus, in accordance with an embodiment of the present invention.

In step 302, specimen 132 is prepared. In this embodiment, specimen 132 is prepared by filling it with liquid and sealing any openings specimen 132 has, such that the liquid contained in specimen 132 does not drain immediately. For example, where specimen 132 is a coiled hose, specimen 132 can be sealed with hose barbs and NPT threaded plugs. In general, specimen 132 can be sealed with any components necessary to prevent water from draining immediately from specimen 132. In this embodiment, the liquid used is water. In other embodiments, other liquids and/or combinations of liquids can be used (e.g., water, dielectric liquids, liquid nitrogen, liquid helium, antifreeze, etc.). For fluids other than water, sensors that measure the concentration of those fluids can be attached to electrical feed through 124.

In step 304, specimen 132 is inserted into moisture leakage measuring apparatus 106. In this embodiment, specimen 132 is inserted to moisture leakage measuring apparatus 106 by unscrewing removable cover 111 and placing specimen 132 inside the compartment of chamber 108. Chamber 108 is sealed after specimen 132 is placed inside its compartment by coupling removable cover 111 over opening 112 and screwing removable cover 111 to chamber 108 using fasteners 114.

In step 306, chamber 108 of moisture leakage measuring apparatus 106 is dried. In this embodiment, moisture leakage measuring apparatus 106 is dried by pumping gas into the compartment of chamber 108 until the compartment of chamber 108 is below desired a percent relative humidity. For example, a desired percent relative humidity may be one that is similar to the relative humidity of the environment in which the specimen will be deployed during use. For example, water-carrying hardware, such as a hose used to cool computer processors, is generally found in data centers whose percent relative humidity may fluctuate around 40% relative humidity. Therefore, chamber 108 can be pumped with gas until the percent relative humidity is about 10-15% below the desired percent relative humidity of 40%.

In step 308, moisture leakage measuring apparatus 106 measures the change in percent relative humidity within chamber 108 over time. In this embodiment, the change in percent relative humidity is measured by RH probe 118 over a specified period of time, such as two weeks. In general, the duration of time a specimen is measured comprises any time period sufficient to gather enough data points around the percent relative humidity of the environment specimen 132 will be deployed. In this embodiment, RH probe 118 measures the change in percent relative humidity by measuring the amount of water loss from specimen 132. Data points are sent to data analysis program 104 via data cable 120.

In step 310, data analysis program 104 calculates a leakage rate of specimen 132 based on measured change of percent relative humidity over a duration of time. For example, the leakage rate may be the rate at which liquid permeates through the specimen over a duration of time, or may be the rate at which liquid leaks between two junctions of the specimen (e.g., between one or more fittings and/or couplings). In this embodiment, moisture leakage measuring apparatus 106 can calculate the leakage rate of the liquid-containing specimen during a period of time as short as two days to two weeks. In this embodiment, data analysis program 104 calculates the leakage rate by the formula reproduced below:

$$P(R)=I(R)*V*K \qquad \text{Formula 1}$$

where P(R) is a daily amount of liquid, expressed in grams, leaked from the specimen at selected relative humidity R; I(R) is a rate of percent relative humidity increase per day at selected relative humidity R; V represents the volume of gas within the chamber when the specimen is disposed within the chamber, expressed in cubic meters; and K represents the product of the density of air times the rate of change of humidity ratio with respect to relative humidity, both quantities evaluated at a given temperature (i.e., the amount of water, expressed in grams, needed to raise the relative humidity of one cubic meter of air by one percent relative humidity at a given temperature (e.g., 22 degrees Celsius).

For example, where P(R) is selected as 40% relative humidity, I(R) is calculated to be 1.06/day, V is 0.00103 m$^3$, K is 0.195 g, data analysis program 104 could use formula 1 to calculate a leakage rate of 0.12 g per day at 40% relative humidity (P(40%)=1.06/day*0.0013 m$^3$*0.195 g).

In this embodiment, data analysis program 104 uses a best fit method to fit the data points to a curve, and calculates I(R) by calculating the slope of the fit at a particular point (e.g., at 40% relative humidity). In this embodiment, data analysis program 104 calculates the fit using an exponential rise to a max for the data points, such that a slope of the fit can be found along any point. In other embodiments, data analysis program 104 can calculate I(R) using a modified hyperbolic fit for the data points. Other embodiments can calculate I(R) by identifying two data points around the percent relative humidity of the environment specimen 132 will be deployed. After identifying two data points, data analysis program 104 calculates the slope (i.e. the change in of between two data points around the desired percent relative humidity) between the two data points. For example, two data points could be (day 10, percent relative humidity 40) and (day 11, percent relative humidity 41.06). Data analysis program 104 calculates the slope by subtracting the change in percent relative humidity (41.06–40) and dividing that total (1.06) by the change in time (Day 11–Day 10) to yield a slope (i.e. change in rate) of 1.06 percent relative humidity per day.

In this embodiment, data analysis program 104 calculates V by subtracting the volume of specimen 132 from the volume of moisture leakage measuring apparatus 106. In this embodiment, the volume of the box is known and calculated as (12−0.75*2)(12−0.0375*2)(2.54)$^3$ to yield a value of 0.02275 m$^3$. In this embodiment, the volume of specimen 132 is known and calculated as ((14)(12)(1.75/2)(2.54)) to yield a value of 0.00103 m$^3$. Data analysis program 104 then subtracts the volume of specimen 132 from the volume of moisture leakage measuring apparatus 106 (0.00276 m$^3$-0.0013 m$^3$) to yield the volume of moisture leakage measuring apparatus 106 of 0.022 m$^3$.

In this embodiment, data analysis program 104 identifies K, which represents the amount of water, expressed in grams, needed to raise the relative humidity of one cubic meter of air by one percent relative humidity at 22 degrees Celsius as 0.195 g.

In step 312, data analysis program 104 calculates leakage over a specified duration of time. In this embodiment, the leakage rate for a desired percent relative humidity can be calculated to take into account different metrics (i.e., different intervals of time or measurements of the specimen). For example, the leakage rate per day can be multiplied by a unit of time, such as 365 days, to yield the leakage rate for one year. The leakage rate could also be divided by another measurement metric, such as the length of a hose, to yield a leakage rate per foot of hose.

Accordingly, by performing the operational steps of FIG. 3, moisture leakage measuring system 100 can be used to calculate the leakage rate of a water-carrying specimen in an efficient and cost-effective manner, without having to create a membrane of material for which moisture leakage is to be tested. The operational steps of FIG. 3 may be repeated for the same water-carrying specimen to determine the cause of leakage. For example, in the first instance, moisture leakage of the water-carrying specimen can be measured when using hose barbs and NPT threaded plugs to seal the water-carrying specimen. In a second instance, the same water-carrying specimen can be measured for moisture leakage, but while using a different set of fittings and/or couplings to seal the water-carrying specimen. The difference between the two measurements shows the leakage attributable to the different fittings and/or couplings.

Figure 4:
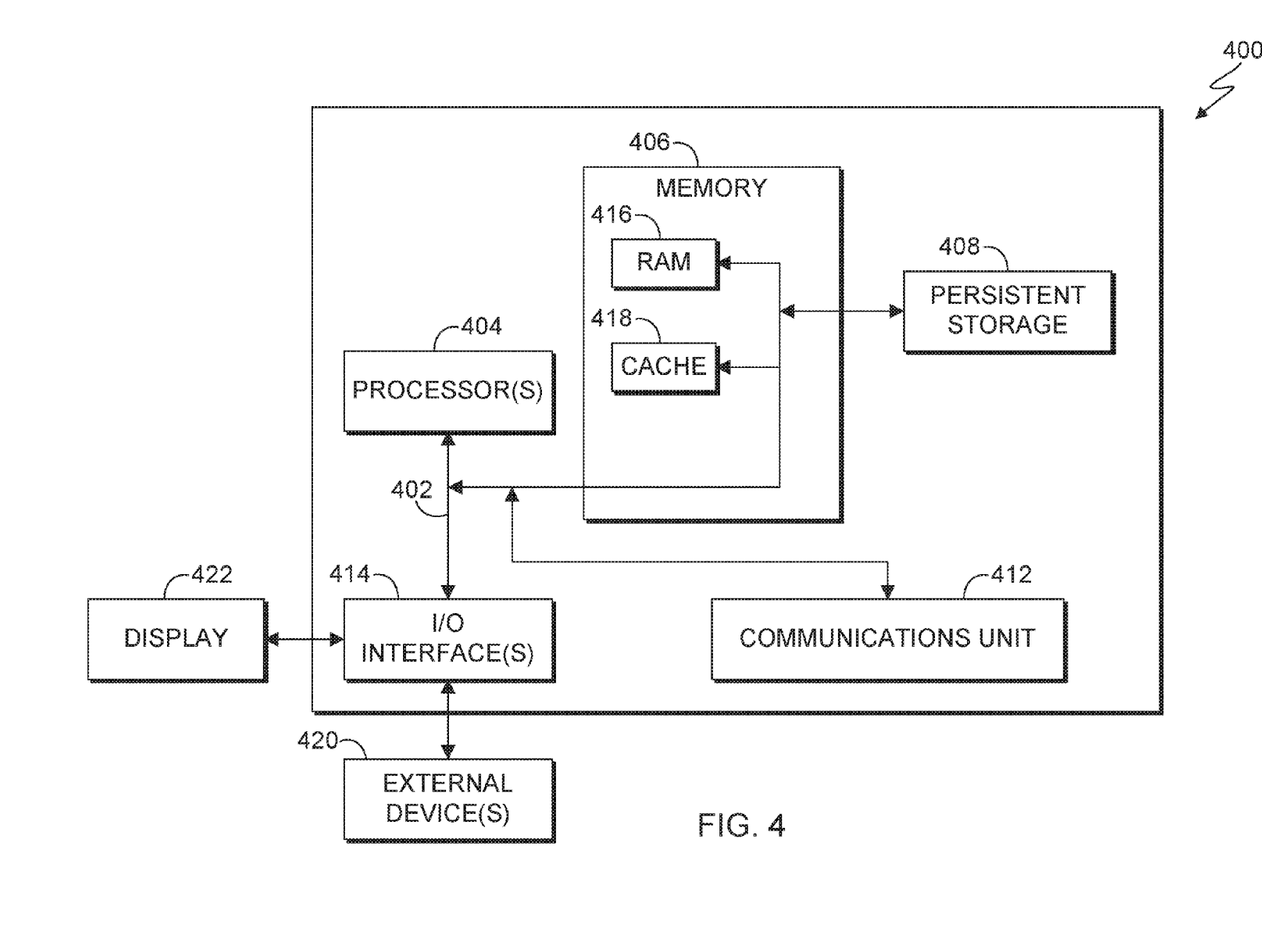
FIG. 4 is a block diagram of internal and external components of the computer systems of FIG. 1, in accordance with an embodiment of the present invention.

FIG. 4 is a block diagram of internal and external components of a computer system 400, which is representative the computer systems of FIG. 1, in accordance with an embodiment of the present invention. It should be appreciated that FIG. 4 provides only an illustration of one implementation and does not imply any limitations with regard to the environments in which different embodiments may be implemented. In general, the components illustrated in FIG. 4 are representative of any electronic device capable of executing machine-readable program instructions. Examples of computer systems, environments, and/or configurations that may be represented by the components illustrated in FIG. 4 include, but are not limited to, personal computer systems, server computer systems, thin clients, thick clients, laptop computer systems, tablet computer systems, cellular telephones (e.g., smart phones), multiprocessor systems, microprocessor-based systems, network PCs, minicomputer systems, mainframe computer systems, and distributed cloud computing environments that include any of the above systems or devices.

Computer system 400 includes communications fabric 402, which provides for communications between one or more processors 404, memory 406, persistent storage 408, communications unit 412, and one or more input/output (I/O) interfaces 414. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406 and persistent storage 408 are computer-readable storage media. In this embodiment, memory 406 includes random access memory (RAM) 416 and cache memory 418. In general, memory 406 can include any suitable volatile or non-volatile computer-readable storage media. Software is stored in persistent storage 408 for execution and/or access by one or more of the respective processors 404 via one or more memories of memory 406.

Persistent storage 408 may include, for example, a plurality of magnetic hard disk drives. Alternatively, or in addition to magnetic hard disk drives, persistent storage 408 can include one or more solid state hard drives, semiconductor storage devices, read-only memories (ROM), erasable programmable read-only memories (EPROM), flash memories, or any other computer-readable storage media that is capable of storing program instructions or digital information.

The media used by persistent storage 408 can also be removable. For example, a removable hard drive can be used for persistent storage 408. Other examples include optical and magnetic disks, thumb drives, and smart cards that are inserted into a drive for transfer onto another computer-readable storage medium that is also part of persistent storage 408.

Communications unit 412 provides for communications with other computer systems or devices via a network. In this exemplary embodiment, communications unit 412 includes network adapters or interfaces such as a TCP/IP adapter cards, wireless Wi-Fi interface cards, or 3G or 4G wireless interface cards or other wired or wireless communication links. The network can comprise, for example, copper wires, optical fibers, wireless transmission, routers, firewalls, switches, gateway computers and/or edge servers. Software and data used to practice embodiments of the present invention can be downloaded to computer system 102 through communications unit 412 (e.g., via the Internet, a local area network or other wide area network). From communications unit 412, the software and data can be loaded onto persistent storage 408.

One or more I/O interfaces 414 allow for input and output of data with other devices that may be connected to computer system 400. For example, I/O interface 414 can provide a connection to one or more external devices 420, such as a keyboard, computer mouse, touch screen, virtual keyboard, touch pad, pointing device, or other human interface devices. External devices 420 can also include portable computer-readable storage media such as, for example, thumb drives, portable optical or magnetic disks, and memory cards. I/O interface 414 also connects to display 422.

Display 422 provides a mechanism to display data to a user and can be, for example, a computer monitor. Display 422 can also be an incorporated display and may function as a touch screen, such as a built-in display of a tablet computer.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method, comprising:
providing a chamber for calculating an amount of liquid leaked by a specimen having one or more walls that define a compartment, wherein the chamber is comprised of one or more materials impermeable to water;
providing a relative humidity probe disposed in a wall of the chamber, wherein at least a portion of the relative humidity probe is disposed within the compartment and is configured to measure relative humidity within the compartment;
providing a first opening disposed in a wall of the chamber, wherein the first opening is configured to receive a hose, and wherein the first opening is further configured to receive a plug to seal the compartment;
providing a second opening disposed in a wall of the chamber for inserting the specimen containing liquid, such that all of the specimen is contained within the compartment, and wherein the specimen containing liquid comprises one or more components of a water cooling hardware system;
providing a removable cover configured to seal the second opening when coupled to the chamber, wherein the removable cover comprises a removable plate coupled to the chamber by one or more fasteners;
providing a computer system operatively connected to the relative humidity probe, wherein the computer system is configured to receive data signals from the relative humidity probe and calculate an amount of liquid leaked by the specimen;
inserting the specimen into the compartment through the second opening, wherein inserting the specimen comprises:
filling the specimen with liquid,
sealing one or more openings of the specimen to contain the liquid within the specimen,
inserting the sealed specimen into the compartment through the second opening,
covering the second opening with the removable cover, and
coupling the removable cover to the chamber;
drying the compartment with one or more gases inputted into the compartment through the first opening, wherein drying the compartment comprises pumping one or more gases into the compartment through a hose inserted into the first opening, such that a percent relative humidity reaches a percent relative humidity of an environment in which the liquid-carrying specimen is used, and sealing the first opening by inserting the plug into the first opening; and
calculating, by the computer system, an amount of liquid leaked by the specimen based on change in percent relative humidity measured by the relative humidity probe, wherein calculating the amount of liquid leaked comprises:
measuring, by the relative humidity probe, changes in percent relative humidity in the compartment over a duration of time;

calculating, by the computer system, a rate of percent relative humidity increase over the duration of time; and calculating, by the computer system, an amount of liquid leaked by the specimen during the duration of time less than or equal to two weeks.

* * * * *